United States Patent [19]

Tregear

[11] 4,086,196

[45] Apr. 25, 1978

[54] PARATHYROID HORMONE

[75] Inventor: Geoffrey William Tregear, Hawthorn, Australia

[73] Assignee: Armour Pharmaceutical Company, Phoenix, Ariz.

[21] Appl. No.: 563,173

[22] Filed: Mar. 28, 1975

[51] Int. Cl.$^2$ .................... C07C 103/52; C08L 37/00
[52] U.S. Cl. .................................. 260/112.5 R; 260/8
[58] Field of Search ............................. 260/112.5 R, 8

[56] References Cited

U.S. PATENT DOCUMENTS 3,886,132  5/1975  Brewer et al. ................ 260/112.5 R

*Primary Examiner*—Delbert R. Phillips
*Attorney, Agent, or Firm*—Richard R. Mybeck; Carl C. Batz

[57] ABSTRACT

A peptide chosen from the group comprising [Ala$^1$]-HPTH-(1-X) and HPTH-(1-X) wherein X is an integer from 27 to 34.

2 Claims, No Drawings

PARATHYROID HORMONE

This invention relates to the synthesis of fragments of parathyroid hormone.

Parathyroid hormone is one of two peptide hormones, the other being calcitonin, which act to regulate and maintain normal levels of serum calcium. The normal action of parathyroid hormone is to mobilize bone calcium to restore balance when there is a deficit of serum calcium.

We have found that all fragments of human parathyroid hormone greater than HPTH-(1-27) and [Ala¹]-HPTH-(1-27) have useful biological properties.

Accordingly we provide a peptide chosen from the group comprising [Ala¹]-HPTH-(1-X) and HPTH-(1-X) wherein X is an integer from 27 to 34.

Preferably the peptide contains 34 residues and accordingly in a preferred aspect of our invention we provide a peptide H-X-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH where X is Ser or Ala.

This peptide where X is Ser is the amino terminal 34 residues of human parathyroid hormone HPTH-(1-34).

The structures of both bovine (Brewer and Rowan, *Proc. Nat. Acad. Sci. USA*, 1970, 67, 1862: Niall, Keutmann, Sauer, Hogan, Dawson, Aurbach, Potts, *Hoppe Seyler's Zeit. Physiol. Chem.*, 1970, 351, 1586) and porcine (Potts, Keutmann, Niall, Tregear, in "Vitamins and Hormones" Vol. 29, p.41 Academic Press, N.Y., 1971) parathyroid hormones have been determined, and the structural requirements for biological activity have been defined in the case of the bovine hormone (Tregear, Rietschoten, Greene, Keutmann, Niall, Reit, Parsons, Potts, *Endcerinology*, 1973, 93, 1349). A synthetic peptide corresponding to 1-34 residues of the bovine parathyroid hormone has been shown to possess qualitatively all the properties of the whole hormone (Potts, Tregear, Keutmann, Niall, Sauer, Deftos, Dawson, Hogan, Aurbach, *Proc. Nat. Acad. Sci. USA*, 1971, 68, 63), and was equipotent with it when tested in bioassay systems in vivo and in vitro. Human parathyroid hormone has recently been isolated and the sequence of the amino-terminal 37 residues determined (Niall et al *Proc. Nat. Acad. Sci. USA*, 1974, 71, 384). The peptide is of use in the treatment of osteoporosis.

The peptides were prepared by the use of the automated solid phase procedure described below.

MATERIALS AND METHODS

Reagents

The purity of the solvents and reagents was regarded as a critical factor in determining the final purity of the synthetic peptide. Methylene chloride was redistilled from anhydrous potassium carbonate immediately prior to use to remove impurities that irreversibly block amino groups under the conditions of the solid-phase synthesis (Brunfeldt and Christensen, *Febs Letters*, 1972, 19, 345). Dimethylformamide was stored over molecular sieve 4A, and triethylamine and anisole were redistilled. The protected amino acids (all except glycine in the L-configuration) were purchased from Beckman Instruments Inc. (Palo Alto, California). The t-butyloxycarboyl (Boc) group was used to protect the α-amino function for all amino acids except $N^G$-tosylarginine, where the amyloxycarbonyl (Aoc) derivative was used because of its increased solubility in methylene chloride. The hydroxyl group of serine was protected as the O-benzyl ether: the side-chain carboxyl groups of glutamic and aspartic acids were protected as their benzyl esters, and the imidazole nitrogen of histidine and the guanidine function of arginine were protected with the tosyl group. The benzyloxycarbonyl group was used to block the ε-amino function of lysine. The histidine and lysine derivatives were regenerated from their dicyclohexylamine salts by treating immediately prior to use in the synthesis with 1N sulfuric acid (1.2 eq). The protected amino acid was extracted into ethyl acetate and, after washing with water and drying over anhydrous sodium sulfate, the ethyl acetate was evaporated to dryness under reduced pressure and the residue was taken up in methylene chloride.

Synthesis

Poly(trifluorochloroethylene-g-(chloromethyl)styrene) resin containing 11% polystyrene and chloromethylated to the extent of 0.13 mmol/g Cl was used as the solid support (Tregear, G. W. (1972) in Chemistry and Biology of Peptides (Meienhofer, J. M., ed) pp. 175–178, Ann Arbor Science Michigan). Boc-phenylalanine was esterified to the resin by refluxing in ethanol for 24 h in the presence of triethylamine according to the procedure described by Merrifield. (Merrifield, R. B., *Biochemistry*, (1964), 3, 1385–1390).

The Boc-phenylalanine resin (19.15 g, 1 mmol Phe) was transferred to the reaction vessel of the Beckman Model 990 Synthesizer, and the peptide chain was assembled using the following program (the number of repetitions and the duration of each operation are given in parentheses). (1) Wash with methylene chloride (3x, 15 min). (2) Prewash with 30% trifluoroacetic acid in methylene chloride (1x, 1.5 min). (3) Boc deprotection with 30% trifluoroacetic acid in methylenechloride (1x, 30 min). (4) Wash with methylene chloride (8x, 15 min). (5) Prewash with 10% triethylamine in methylene chloride (2x, 1.5 min). (6) Neutralization with 10% triethylamine in methylene chloride (1x, 10 min). (7) Wash with methylene chloride (5x, 1.5 min). (8) Addition of Boc amino acid (3.0 mmol) in methylene chloride (1x, 10 min). (9) Addition of dicyclohexylcarbodiimide (3.0 mmol) in methylene chloride (1x, 60 min). (10) Wash with methylene chloride (5x, 1.5 min).

Glutamine and asparagine were coupled as their p-nitrophenyl esters. The active ester program differed from the above from step 7 as follows: (7a) Wash with methylene chloride (3x, 1.5 min). (8a) Wash with dimethylformamide (5x, 1.5 min). (9a) Addition of Boc-amino acid active ester (6.0 mmol) in dimethylformamide (1x, 140 min). (10a) Wash with dimethylformamide (5x, 1.5 min).

At the completion of each coupling step a sample of resin was removed and tested for completion of reaction by the ninhydrin procedure. (Kaiser, E., Colescott, R. L. Bossinger, C. D. and Cook, P. I., Anal. Biochem, (1970), 34, 595–598). In the event of a positive or borderline test the coupling reaction was repeated by returning to step 5 in the appropriate program. After the incorporation of tryptophan at residue 23, 1% mercaptoethanol was added to the trifluoroacetic acid reagent and also to the methylene chloride washes following deprotection. This reagent, being unstable, was made up fresh each day. At the completion of the stepwise amino acid additions the peptide was cleaved from the resin with simultaneous removal of the side-chain-protecting groups, by treatment with hydrogen fluoride for 1 h at 0° C in the presence of anisole using the experimental procedure described by Stewart and Young (Solid Phase Peptide Synthesis, Freeman Publ. Comp. San Francisco (1969). The peptide/resin mixture was washed thoroughly with anhydrous ether to remove excess anisole and the peptide was extracted into dilute acetic acid and lyophilized.

The yield of crude peptide obtained from 12.7 g of resin/peptide was 1.65 g. A portion of the resin/peptide (1.5 g) was removed from the reaction vessel after coupling valine at position 2, and in a separate experiment, alanine was coupled to the resin to prepare the [Ala$^1$]-HPTH-(1-34) analogue. The Ala$^1$-peptide was purified and characterised using methods similar to those described below.

Purification

Preliminary purification of the crude peptide was performed by gel filtration on Bio-Gel P6 (Bio-Rad, 100-200 mesh) in 1M acetic acid. The fractions eluted at a Kd between 0.2 and 0.3, representing the major peak of optical density at 280 nm, were combined and lyophilized. The peptide was further purified by chromatography on carboxymethylcellulose (Whatman CM-52) in the presence of 8M urea. A linear gradient was developed using 0.01M ammonium acetate (pH 5.1, conductivity 2.0 mmho) and 0.1M ammonium acetate (pH 6.2, conductivity 8.0 mmho). The buffers were made up in 8M urea which had been freshly prepared and passed through a Rexyn I-300 mixed-bed deionizing resin (Fisher Scientific) to remove traces of cyanate or other ions. For chromatography of a 125-mg sample, a 300 × 20-mm column of CM-52 was used, and the gradient developed using a Varigrad gradient maker (Buchler Instruments) with 2 × 400 ml of low conductivity buffer and 1 × 400 ml of high conductivity buffer. At the conclusion of the gradient 1.0M ammonium acetate in 8M urea (pH 6.9, conductivity 35 mmho) was introduced to clear any remaining peptide from the column. The column effluent was monitored by reading the optical density at 280 nm with a Beckman DBG spectrophotometer. Buffer conductivity was measured at room temperature on a Radiometer CDM-2e conductivity meter calibrated to read in the range 0-50 mmho. The major peptide peak eluted at a conductivity of 4.3 to 4.8 mmho.

A portion of the major peak from the urea-CMC column was rechromatographed on CM-52 using a urea-free ammonium acetate buffer gradient from 1.5 to 15.0 mmho. In the absence of urea the peptide eluted at a conductivity of 10.5 to 12.0 mmho. Samples were desalted where necessary by gel filtration on Bio-Gel P-2 (Bio-Rad, 100-200 mesh) equilibrated in 0.1M acetic acid. All chromatography columns were run at room temperature using a gravity-flow rate of 30-60 ml/hr. Gel filtration of the crude peptide followed by ion-exchange chromatography proved to be a satisfactory procedure for purifying the crude peptide. The yield of purified synthetic HPTH-(1-34)-peptide based on the yield of crude peptide recovered after cleavage from the resin was 10.5%.

CHEMICAL CHARACTERIZATION

Acid hydrolysis was carried out in 5.7 N HCl at 110° C in an evacuated desiccator for 24 h. Mercaptoethanol (1:2000 v/v) was added to each sample to protect methionine residues. (Keutmann, H. T. & Potts Jr., J. T., *Anal Biochem.* (1969) 29, 175-185). Total enzymatic digestion (Keutmann, H. T., Parsons, J. A., Potts Jr., J. T., & Schlueter, R. J., *J. Biol. Chem.*, (1970) 245, 1491-1496) was performed by treating the peptide (100 μg) with papain (5 μg) in ammonium acetate buffer (0.05M, pH 5.35) and in the presence of mercaptoethanol (5 μl, 1:32 solution in water) for 2 h at 37° C. Following the incubation two drops of glacial acetic acid were added and the mixture was lyophilized. The residue was dissolved in trimethylamine/acetic acid buffer pH 8.2 (80 μl) and mercaptoethanol (5 μl) followed by addition of aminopeptidase M (150 μg). After incubation for 3 h at 37° C, two drops of glacial acetic acid were added and the mixture was lyophilized. Amino acid analyses were carried out using the Beckman Model 121 automatic amino acid analyzer. A lithium citrate buffer system (Benson Jr., J. V., Gordon, M. J., & Patterson, J. A., *Anal. Biochem.*, (1967), 18, 228-240) was used to distinguish asparagine, glutamine, aspartic acid and glutamic acid following the enzymatic digestion.

The homogeneity of the synthetic peptides was checked by thin layer chromatography on cellulose (Brinkmann Celplate-22, Eastman 6065) and silica gel (Merck) plates. The samples load was 30 μg in 5 μl of 0.1M acetic acid. The following solvent systems were used: $R_F^a$, n-butanol/acetic acid/water 4:1:5; $R_F^b$, ethyl acetate/pyridine/acetic acid/water 5:5:1:3; $R_F^c$, n-butanol/pyridine/acetic acid/water 15:10:3:12; $R_F^d$, n-butanol/acetic acid/water/ethyl acetate 1:1:1:1. The peptide spots were visualized by spraying the plates with Ehrlich reagent and 0.5% ninhydrin in ethanol. The amino acid composition of the peptide after acid hydrolysis and total enzymatic digestion was in close agreement with theoretical as shown in Table 1. The amino acid residues obtained after enzymatic digestion also established that there was negligible contamination of the purified peptide with side-chain protected amino acids. The purified synthetic HPTH-(1-34)-peptide gave a single spot on thin-layer chromatography with $R_F^a$ (cellulose, Brinkmann) 0.19; $R_F^b$ (silica) 0.11; $R_F^c$ (silica) 0.17; $R_F^c$ (cellulose, Brinkmann) 0.40; $R_F^c$ (cellulose Eastman 6065) 0.66; and $R_F^d$ (cellulose, Brinkmann) 0.48.

Bioassays

In vitro bioassays based on the activation of adenylate cyclase in rat renal cortical homogenates were carried out by the procedure of Marcus and Aurbach (*Endocrinology*, (1969), 85, 801-810). In vivo bioassays were performed by the method of Parsons, Reit and Robinson (*Endocrinology*, (1973), 92, 454-462), a procedure based on increase in the serum calcium in the chick after intravenous injection. A house standard of highly purified bovine parathyroid hormone ("Sephadex-BPTH") calibrated against Medical Research Council Standard A (National Institute for Medical Research, London, England) was used for both in vivo and in vitro assays. The biological activities of the synthetic HPTH-(1-34), and the native HPTH-(1-84)-peptides in the in vitro rat kidney adenylate cyclase assay and the in vivo chick hypercalcemia assay are shown in Table 2. Included for comparison are the corresponding data on the native bovine-(1-84) and the synthetic bovine-(1-34) peptides, as well as the analogue [Ala$^1$]-HPTH-(1-34).

TABLE 1

Amino acid composition of synthetic human 1-34 fragment

| Amino Acid | Theoretical | Acid[a] Hydrolysis | Molar Ratios Enzymatic[b] Hydrolysis |
|---|---|---|---|
| Aspartic acid | 1) | 4.20 | 1.15 |
| Asparagine | 3) |  | 3.08 |
| Serine | 3 | 2.74 | 2.85 |
| Glutamic acid | 3) | 5.32 | 3.03 |
| Glutamine | 2) |  | 2.27 |
| Glycine | 1 | 1.08 | 1.10 |
| Valine | 3 | 2.93 | 2.50 |
| Methionine | 2 | 1.94 | 1.92 |
| Isoleucine | 1 | 0.92 | 0.87 |
| Leucine | 5 | 5.40 | 5.31 |
| Phenylalanine | 1 | 0.94 | 0.98 |
| Tryptophan | 1 | — | 0.86 |
| Lysine | 3 | 3.09 | 3.30 |
| Histidine | 3 | 2.99 | 2.77 |
| Arginine | 2 | 1.94 | 1.93 |

[a]Average of six separate hydrolyses with 5.7N HCl at 110° C for 24 h.
[b]Average of two separate enzymatic digestions.

TABLE 2

Biological activity of native and synthetic human (HPTH) and bovine (BPTH) parathyroid hormone peptides

|  | In vitro Rat kidney adenylate cyclase (MRCU/mg) | In vivo Chick hyper-calcemia (MRCU /mg) |
|---|---|---|
| HPTH-(1-84) (native) | 350 (275-425)[a] | — |
| HPTH-(1-34) | 1030 (930-1140) | 7400(5700-9700) |
| BPTH-(1-84) (native) | 3000(2500-4000) | 2500(2100-4000) |
| BPTH-(1-34) | 5400(3900-8000) | 7700(5200-11100) |
| [Ala¹]-HPTH-(1-34) | 4085(3550-4700) | 4600(3500-6000) |

[a]Values expressed as mean potency with 95% confidence limits.

I claim:

1. A synthetic polypeptide of the formula

H-X-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-QOH where
X is Ser or Ala and
Q is
-Lys-
-Lys-Leu-
-Lys-Leu-Gln-
-Lys-Leu-Gln-Asp-
-Lys-Leu-Gln-Asp-Val-
-Lys-Leu-Gln-Asp-Val-His-
-Lys-Leu-Gln-Asp-Val-His-Asn- or
-Lys-Leu-Gln-Asp-Val-His-Asn-Phe-.

2. A synthetic peptide of the formula

H-X-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH where X is Ser or Ala.

* * * * *